(12) United States Patent
Dowiasch et al.

(10) Patent No.: US 8,974,173 B2
(45) Date of Patent: Mar. 10, 2015

(54) APPARATUS AND PROCESS FOR PROVIDING ARRAYS OF ABSORBENT ARTICLES IN VARYING ORIENTATIONS FOR PACKAGING

(71) Applicant: The Procter & Gamble Company, Cincinnati, OH (US)

(72) Inventors: Michael Jan Dowiasch, Euskirchen (DE); Thomas Luebcke, Euskirchen (DE); Andre Josephine Karel De Saert, Hamme (BE); Hilde Cloostermans, Hamme (BE)

(73) Assignee: The Procter & Gamble Plaza, Cincinnati, OH (US)

( * ) Notice: Subject to any disclaimer, the term of this patent is extended or adjusted under 35 U.S.C. 154(b) by 154 days.

(21) Appl. No.: 13/713,118

(22) Filed: Dec. 13, 2012

(65) Prior Publication Data

US 2013/0156536 A1 Jun. 20, 2013

(30) Foreign Application Priority Data

Dec. 14, 2011 (EP) .................................. 11193490

(51) Int. Cl.
| | |
|---|---|
| B65B 27/08 | (2006.01) |
| B65H 33/00 | (2006.01) |
| B65G 57/00 | (2006.01) |
| B65H 29/66 | (2006.01) |
| A61F 13/551 | (2006.01) |
| A61F 13/15 | (2006.01) |

(52) U.S. Cl.
CPC ............... *B65G 57/00* (2013.01); *B65B 27/08* (2013.01); *B65H 29/66* (2013.01); *B65H 2301/33224* (2013.01); *A61F 13/55115* (2013.01); *A61F 13/15747* (2013.01)
USPC ........................................ 414/791.2; 198/374

(58) Field of Classification Search
USPC ............................ 198/374, 418.4, 429, 439; 271/184–186, 302, 65, 903; 414/791.1, 414/791.2, 791.3, 791.4, 798.4, 798.6, 414/798.7; 53/152, 158, 447, 540
See application file for complete search history.

(56) References Cited

U.S. PATENT DOCUMENTS

| | | | | | |
|---|---|---|---|---|---|
| 2,182,880 | A | * | 12/1939 | Roberts | 414/798.4 |
| 3,593,624 | A | * | 7/1971 | Dufour | 414/788.3 |
| 4,065,117 | A | * | 12/1977 | Thorsheim | 270/52.02 |
| 4,307,800 | A | * | 12/1981 | Joa | 198/374 |
| 4,856,768 | A | * | 8/1989 | Hiroki et al. | 271/186 |
| 5,897,292 | A | | 4/1999 | Gerwe et al. | |
| 6,746,202 | B2 | * | 6/2004 | Mader et al. | 414/788.3 |
| 7,624,855 | B2 | * | 12/2009 | Martocchio et al. | 198/405 |

(Continued)

FOREIGN PATENT DOCUMENTS

| | | |
|---|---|---|
| EP | 0030653 B1 | 9/1983 |
| EP | 0780325 A1 | 6/1997 |

(Continued)

OTHER PUBLICATIONS

International Search Report, PCT/US2012/069466, mailed Feb. 26, 2013, 10 pages.

*Primary Examiner* — Gregory Adams
(74) *Attorney, Agent, or Firm* — Andrew A Paul

(57) ABSTRACT

Apparatus for producing arrays of absorbent articles with varying orientations, and a methods for forming alternating arrays of absorbent articles, suitable to be operated at a high speed, are provided.

13 Claims, 13 Drawing Sheets

(56) References Cited

U.S. PATENT DOCUMENTS 7,681,374 B2 * 3/2010 Schulte et al. ............... 53/143
2005/0229543 A1 10/2005 Tippey
2010/0071318 A1 * 3/2010 Brandhorst et al. ........... 53/446

FOREIGN PATENT DOCUMENTS

| WO | WO 99/61359 A1 | 12/1999 |
|----|----------------|---------|
| WO | WO 0035776 A1 | 6/2000 |

* cited by examiner

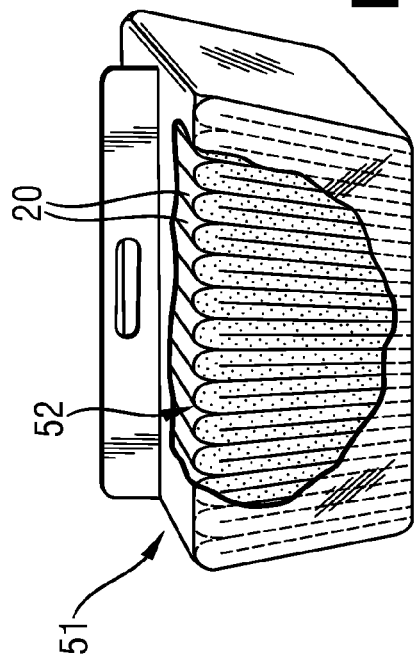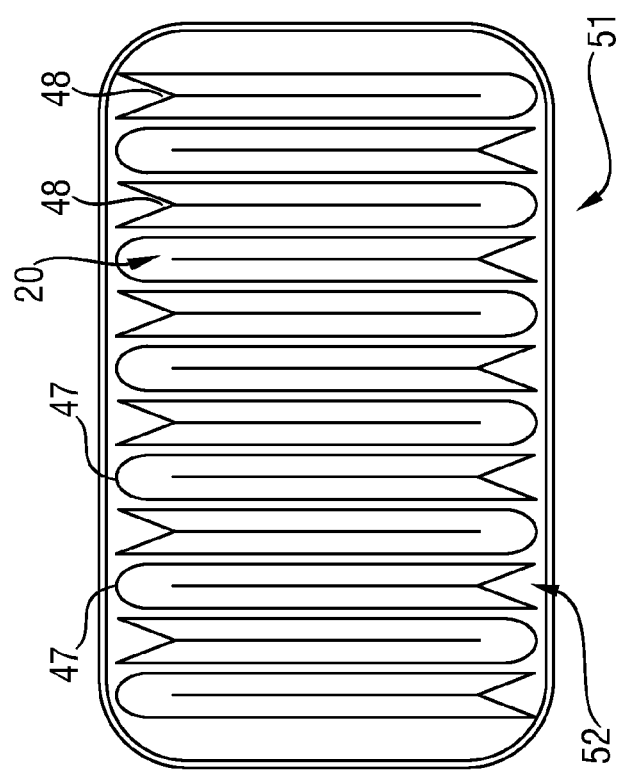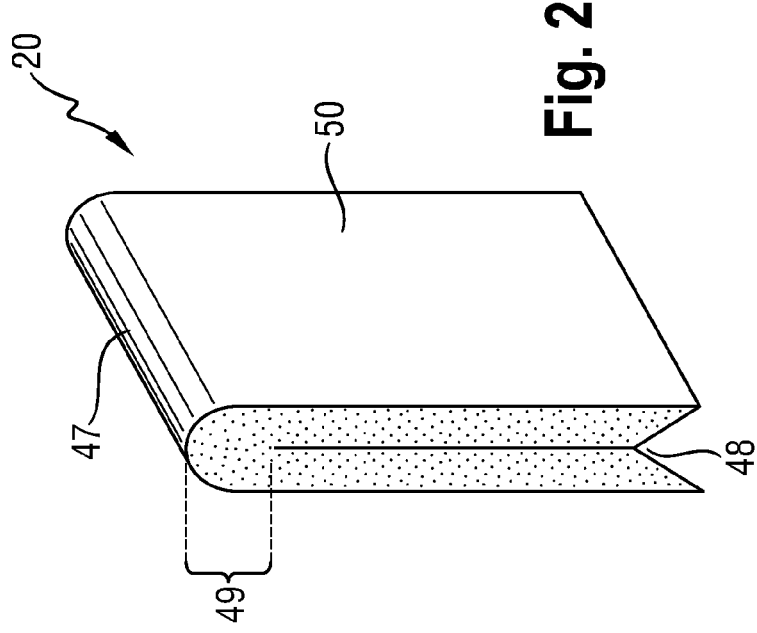

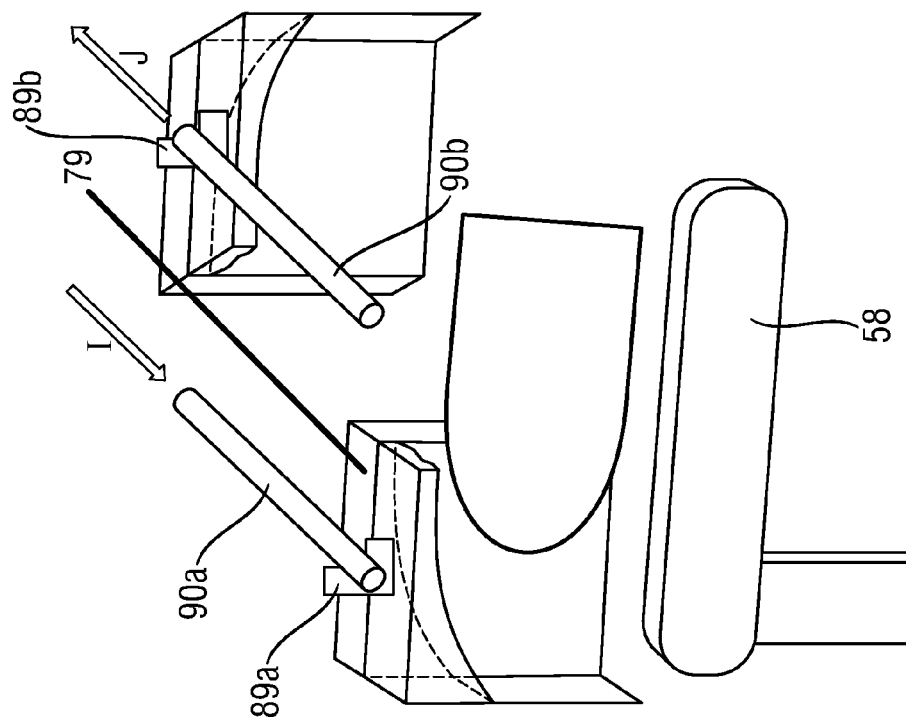
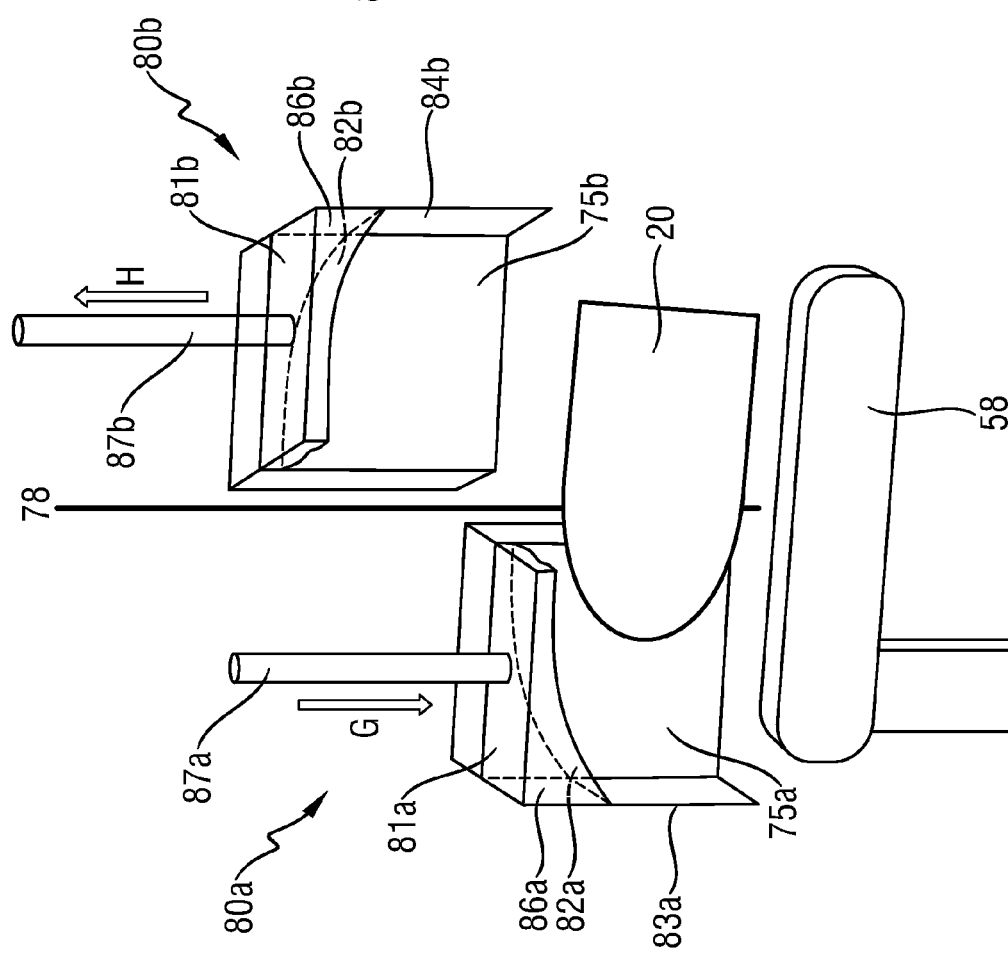

APPARATUS AND PROCESS FOR PROVIDING ARRAYS OF ABSORBENT ARTICLES IN VARYING ORIENTATIONS FOR PACKAGING

FIELD OF THE INVENTION

The present invention relates to an apparatus and process for forming arrays of absorbent articles for subsequent packaging. More particularly, the present invention provides an apparatus and a method for forming arrays wherein the absorbent articles are positioned in varying orientations, such as in alternating orientation.

BACKGROUND OF THE INVENTION

Many absorbent articles such as diapers have a non-rectangular shape, and thus the packaging of these irregular items can be problematic. If these products are not packaged in an optimal manner, package strength and integrity may suffer. Indeed, if the resulting package is not substantially rectangular, it may lead to undesirable unstable package on a pallet. It is also usually desirable to load as many articles as possible into a package of a given size in order to minimize slack space and for cost savings in packing material and logistic cost savings. When the absorbent articles are not uniform in size or shape, optimal packaging may make it desirable that the absorbent articles be packaged in an alternating manner.

In some prior art methods, the absorbent articles within an array are arranged in an alternating orientation. For instance, European Patent EP 0030653 B1, International Patent Application WO 99/61359 A1 and U.S. Pat. No. 5,897,292 refer to processes for forming arrays of absorbent articles in varying orientations, such as in alternating orientation for subsequent packaging. However, these processes are rather space consuming in the manufacturing line and/or require expensive apparatus.

There is therefore a need to provide a simpler and cost-efficient apparatus and a process for producing arrays of absorbent articles in varying orientations, such as in alternating orientation. Also, the apparatus and process should allow for high speed manufacture. There is also a desire to provide an apparatus which does not accommodate too much space in the manufacture line or which enables a more flexible set-up, to be able to adapt to certain space constraints at the manufacturing line.

SUMMARY OF THE INVENTION

It is an object of the present invention that one or more embodiments provide an apparatus for producing arrays of absorbent articles with varying orientations.

In some aspects, the invention concerns processes for forming alternating arrays of absorbent articles, suitable to be operated at a high speed, which means that hundreds of absorbent articles may be alternately packed per minute.

The process comprises the steps of:
(a) advancing the absorbent articles along a predetermined (or incoming) path,
(b) diverting the absorbent articles by using a diverter, wherein a first plurality of absorbent articles is routed to a first path and a second plurality of absorbent articles is routed to a second path, wherein the first and second path have a direction different from each other,
(c) providing the first and second plurality of absorbent articles to a stacker, wherein the stacker is able to receive the absorbent articles from the first and second path,
(d) forming an array of absorbent articles from the first and second plurality of absorbent articles in the stacker, wherein one or more than one of the absorbent articles has a first orientation and one or more than one of the absorbent articles has a second orientation within the array, the first and second orientation being different from each other,
(e) advancing the array of absorbent articles along a third path, which has a direction different from the direction of the first and the second path.

Another process of diverting absorbent articles comprises the steps of:
(a) advancing the absorbent articles along a predetermined (or incoming) path,
(b) diverting the absorbent articles by using a diverter, wherein a first plurality of absorbent articles is routed to a first path and a second plurality of absorbent articles is routed to a second path, wherein the first and second path have a direction different from each other,
wherein the first and second path take a substantially diverging direction along a first distance onto a guide roll and subsequently take a substantially convergent direction along a second distance behind the guide roll.

Another process of forming arrays of absorbent articles with varying orientations comprises the steps of:
(a) providing a stacker, the stacker comprising a plurality of paddles placed at equal distances for receiving the absorbent articles,
(b) opening up two neighboring paddles by bending outwardly at least one of the paddle,
(c) introducing the absorbent articles delivered from two substantially opposite directions onto the stacker,
d) stopping the absorbent article by an infeed plate, wherein the infeed plate is:
  i) pivoting, or
  ii) comprising a first and second parts, the first and second parts sliding up and down, or back and forth,
(e) closing the neighboring paddles by straightening at least one paddle relative of its neighbor,
(f) forming an array of absorbent articles by repeating steps b-e.

An apparatus for performing the above process comprises:
(a) a conveyor for advancing the absorbent articles,
(b) a diverter for diverting the absorbent articles to route a first plurality of absorbent articles to a first path and a second plurality of absorbent articles to a second path, wherein the first and second path have a direction different from each other,
(c) a stacker for receiving the first and second plurality of absorbent articles, which are delivered along the first and second path, wherein the stacker can form an array of absorbent articles from the first and second plurality of absorbent articles, such that one or more than one of the absorbent articles has a first orientation and one or more than one of the absorbent articles has a second orientation within the array, the first and second orientation being different from each other,
(d) a conveyor for advancing the array of absorbent articles along a third path, which has a direction different from the direction of the first and second path.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

FIG. 2 is a perspective view of a bi-folded absorbent article;

FIG. 3 shows a package comprising an array of absorbent articles in a non-alternating, side by side orientation;

FIG. 4 is a schematic view of a package of absorbent articles comprising an array formed by using the apparatus and methods of the present invention;

FIG. 12A is a schematic view of an infeed plate which consist of first and second part that may slide up and down, and which are above a paddle secured to a stacker;

FIG. 12B is a schematic view of an infeed plate which consist of first and second part that may slide back and forth, and which are above a paddle secured to a stacker;

DETAILED DESCRIPTION OF THE INVENTION

Definition of Terms

Figure 1:
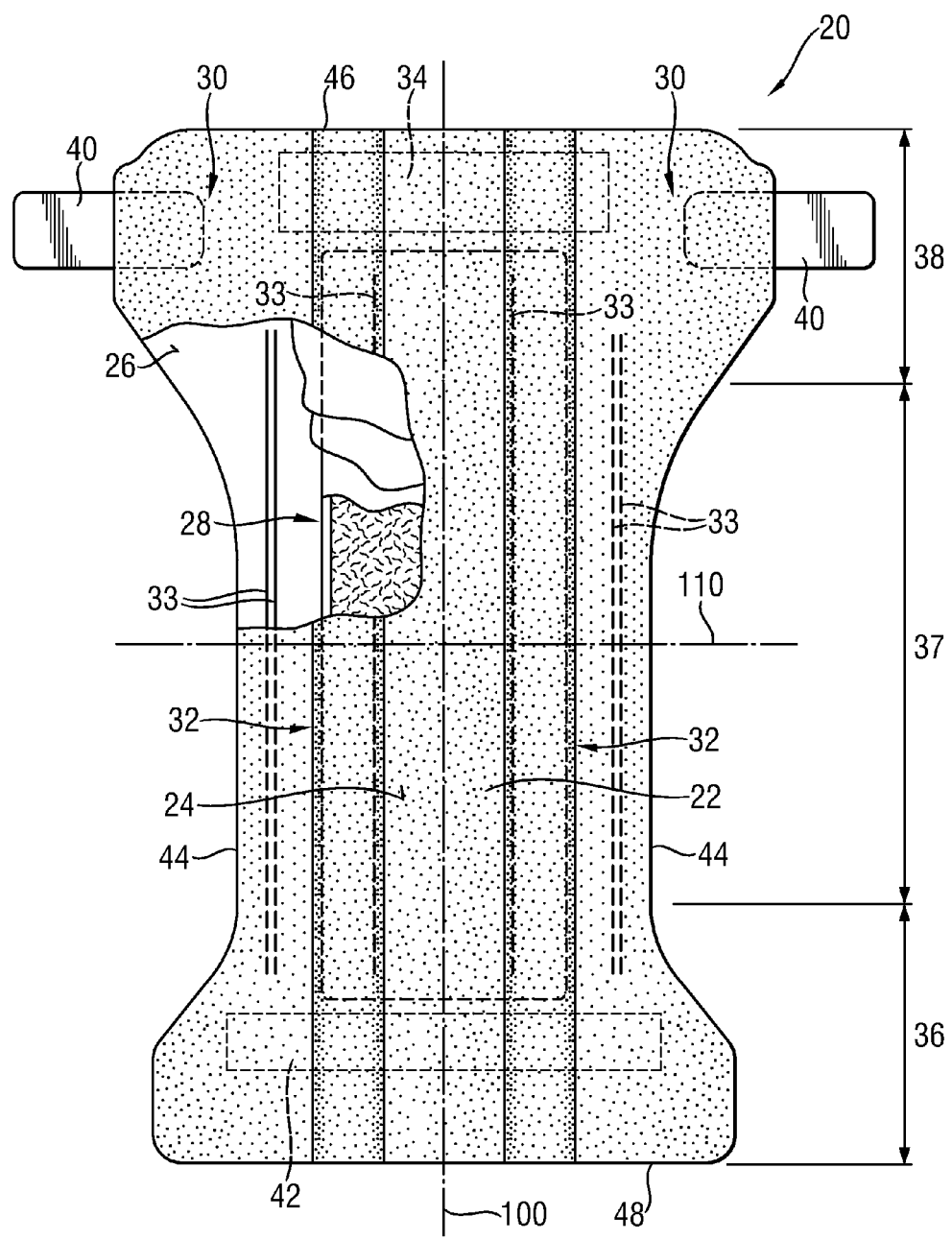
FIG. 1 shows a diaper as an exemplary embodiment of an absorbent article.

The term "absorbent article" as used herein refers to an article placed against or in proximity to the body of the wearer to absorb and contain the exudates discharged from the body. Typical absorbent articles of the present invention are diapers, adult incontinence briefs, absorbent inserts and the like, as well as feminine hygiene products, such as sanitary napkins and panty liners.

"Diaper" as used herein refers to an absorbent article that is intended to be worn by a wearer about the lower torso to absorb and contain exudates discharged from the body.

Diapers may be worn by infants (e.g. babies or toddlers) or adults. They may be provided with fastening elements. Alternately, they may be in pant form having permanently bonded or releasably prefastened side panels to form leg openings. Pant-like diapers are placed in position on the wearer by inserting the wearer's legs into the leg openings and sliding the pant-like diaper into position about the wearer's lower torso.

"Comprise," "comprising," and "comprises" as used herein is an open ended term that specifies the presence of what follows e.g. a component but does not preclude the presence of other features, elements, steps or components known in the art, or disclosed herein.

"Diverter" as used herein is a component of the apparatus for forming the arrays of absorbent articles with varying orientations. The "diverter" facilitates the separation of absorbent articles and redirects them to a first and second paths. The first and second paths may have a different direction from the incoming path to the diverter.

"Stacker" as used herein is a device for forming arrays of items such as absorbent articles. A stacker may be a stacker chain that may operate on a rail-like structure with movable wheels and comprise a plurality of paddles secure on it. A stacker may alternatively comprise other types of compartments such as cassettes, which include a number of opposing paddles placed at equal distances in fixed positions relative to the outer casing of the cassette and that define a receiving space therebetween.

"Paddle" as used herein is a component of a stacker used to support and separate absorbent articles while the array of absorbent articles is formed. The absorbent articles may be held between the paddles until the array of absorbent articles is inserted in a package.

"Infeed plate" as used herein is another component of a stacker. It refers to a tool used to guide and stop an absorbent article delivered between an adjacent pair of paddles.

"Pivoting" as used herein refers to the following repetitive rotation of the infeed plate:

a) around an axis that is perpendicular to and passes through an upper surface of the infeed plate and preferably rotates at an angle γ ranging from −40 degrees to +40 degrees, or from −30 degrees to +30 degrees, or from −20 degrees to +20 degrees, or b) around an axis that is perpendicular to and passes through a front surface of an upper protrusion or a main surface of the infeed plate and preferably rotates at an angle δ ranging from −90 degrees to +90 degrees, or from −80 degrees to +80 degrees, or from −70 degrees to +70 degrees.

"Sliding" as used herein refers to a repetitive movement of infeed plates which consist of first and second parts, wherein:

a) the first and second parts of infeed plate may slide back and forth. When the first part of infeed plate slides back, the second part of infeed plate slides forth, or b) the first and second parts of infeed plate may slide up and down. When the first part of infeed plate slides up, the second part of infeed plate slides down.

"Twisting" as used herein refers to motion to bring an absorbent article from a horizontal into a vertical position.

"Guide roll" as used herein redirects an absorbent article which may be provided on a conveyor belt.

Exemplary Absorbent Articles

FIG. 1 is a plan view of a diaper 20 as an embodiment of an absorbent article. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer.

The diaper 20 has a length along a longitudinal axis 100 and a width along a transverse axis 110. The periphery of the diaper 20 is defined by the outer edges of the diaper 20 in which the longitudinal edges 44 run generally parallel to the longitudinal axis 100 of the diaper 20 and the end edges 46 and 48 run generally parallel to the transverse axis 110 of the diaper 20.

The chassis 22 of the diaper 20 in FIG. 1 comprises the main body of the diaper 20. The chassis 22 comprises an outer covering including a liquid pervious topsheet 24 and/or a liquid impervious backsheet 26. The entire absorbent core 28 is encased between the topsheet 24 and the backsheet 26.

Optionally, the diaper 20 comprises an acquisition system to acquire and temporarily store fluids discharged from the body. Such an acquisition system may be deposited between the absorbent core 28 and the topsheet 24.

The chassis 22 may further include side panels 30, leg cuffs 32 with elastic members 33 and a waist feature 34. The leg cuffs 32 and the waist feature 34 typically comprise elastic members.

One end portion of the diaper is configured as the front waist region 36 of the diaper 20. The opposite end portion is configured as the rear waist region 38 of the diaper 20. The intermediate portion of the diaper is configured as the crotch region 37, which extends longitudinally between the front and rear waist regions. The crotch region 37 is that portion of the diaper 20 which when the diaper is worn, is generally positioned between the wearer's legs.

The waist regions 36 and 38 may include a fastening system comprising fastening members 40 preferably attached to the rear waist region 38 and a landing zone 42 attached to the front waist region 36. Alternatively, the rear waist region may be permanently bonded to the front waist region to form a pant-type diaper having a waist opening and two leg openings.

The diaper may also include other features that are known in the art including front and rear ear panels, waist cap features, elastics and the like to provide better fit, containment and aesthetic characteristics.

FIG. 2 is a perspective view of a bi-folded absorbent article 20 such as a diaper. However, a bi-folded absorbent article for the apparatus and processes of the present invention may also be a bi-folded feminine hygiene product, such as a bi-folded sanitary napkin or a bi-folded panty liner. The absorbent article may be bi-folded in its crotch region along or adjacent to the transverse axis 110 (See FIG. 1). The edge 47 formed at the fold in the crotch region is hereafter referred to as "nose" of the absorbent article. The edge 48 where the front and the rear waist regions are folded onto each other is hereinafter referred to as the "tail" of the absorbent article. The "main surface 50" of bi-folded absorbent article 20, as shown in FIG. 2 is facing outwardly and encompasses the region between the waist region to the folded crotch region 49. Consequently, a bi-folded absorbent article has two main surfaces. In a "horizontal position" of an absorbent article, as used herein, the main surface 50 is horizontal. In a "vertical position" of an absorbent article, as used herein, the main surface 50 is vertical.

The absorbent article may alternatively be tri-folded. Tri-folded absorbent articles may comprise tri-folded diapers and tri-folded feminine hygiene products. In a tri-folded absorbent article, the first waist region is folded over the crotch region along a fold line parallel to the transverse axis, followed by folding the second waist region over the folded first waist region. Similar to a bi-folded absorbent article, a tri-folded absorbent article has also two main surfaces, facing outwardly.

Bi-folded absorbent articles are often profiled with a nose (Typically, the whole folded crotch region is thicker.) thicker than the tail, as the absorbent core of many absorbent articles does not extend over the whole length of the article onto the waist edges. FIG. 3 shows a package 51 comprising an array 52 of bi-folded absorbent articles 20. The flexible package 51 maintains the array 52 of bi-folded absorbent articles. The package 51 may comprise a thermoplastic bag of flexible film, as it is known in the art. When arrays having aligned absorbent article orientations (e.g. noses positioned adjacent each other) are obtained, this results in one edge of the array being thicker than the other, thereby resulting in inefficient and unstable packaging.

FIG. 4 is a top plan, schematic view of a package 51 having an array 52 of absorbent articles 20 produced using the apparatus and processes of the present invention. The package 51 typically comprises a flexible polymeric film. The package 51 may also contain a plurality of arrays 52, one placed on top of the other or next to each other. The arrays have been compiled using the apparatus and methods of the present invention. The absorbent articles of the array are provided in alternating orientations. In other words, the nose 47 of a bi-folded absorbent article is positioned next to the tail 48 of an adjacent bi-folded absorbent article. The configuration of array 52 in FIG. 4 largely eliminates variations in the thickness of an array of absorbent articles, leading to a more homogeneous and relatively rectangular shape.

The result is that the package size can be reduced for a given number of absorbent articles, or, alternatively, more absorbent articles can be fitted into a package of given size, since arrays of absorbent articles in the alternating orientation of FIG. 4 can be more densely packed within a rectangular package than those having an aligned orientation. This leads to cost savings in packing material and also to logistic cost savings. Package appearance is also improved with a rectangular package. A rectangular package is more stable on a pallet.

In addition, it is not essential that every absorbent article has an alternating orientation relative to the neighboring absorbent article. The absorbent articles in the array may be arranged in "subunits". The absorbent articles in each individual subunit are then oriented with their nose 47 at the same side. Each subunit may consist of two absorbent articles. In alternative configurations, each subunit may consist of three, four or more absorbent articles, in which all the absorbent articles in each subunit are oriented in the same direction. Every subunit in an array has an alternating orientation relative to the neighboring subunit. These configurations also result in an overall relative rectangular shape of the array absorbent articles. Also, subunits within an array of absorbent articles may consist of different numbers of absorbent articles, such as a subunit with two absorbent articles alternating with a subunit of only one, or three absorbent articles.

Advancing and Diverting the Absorbent Articles

Figure 5:
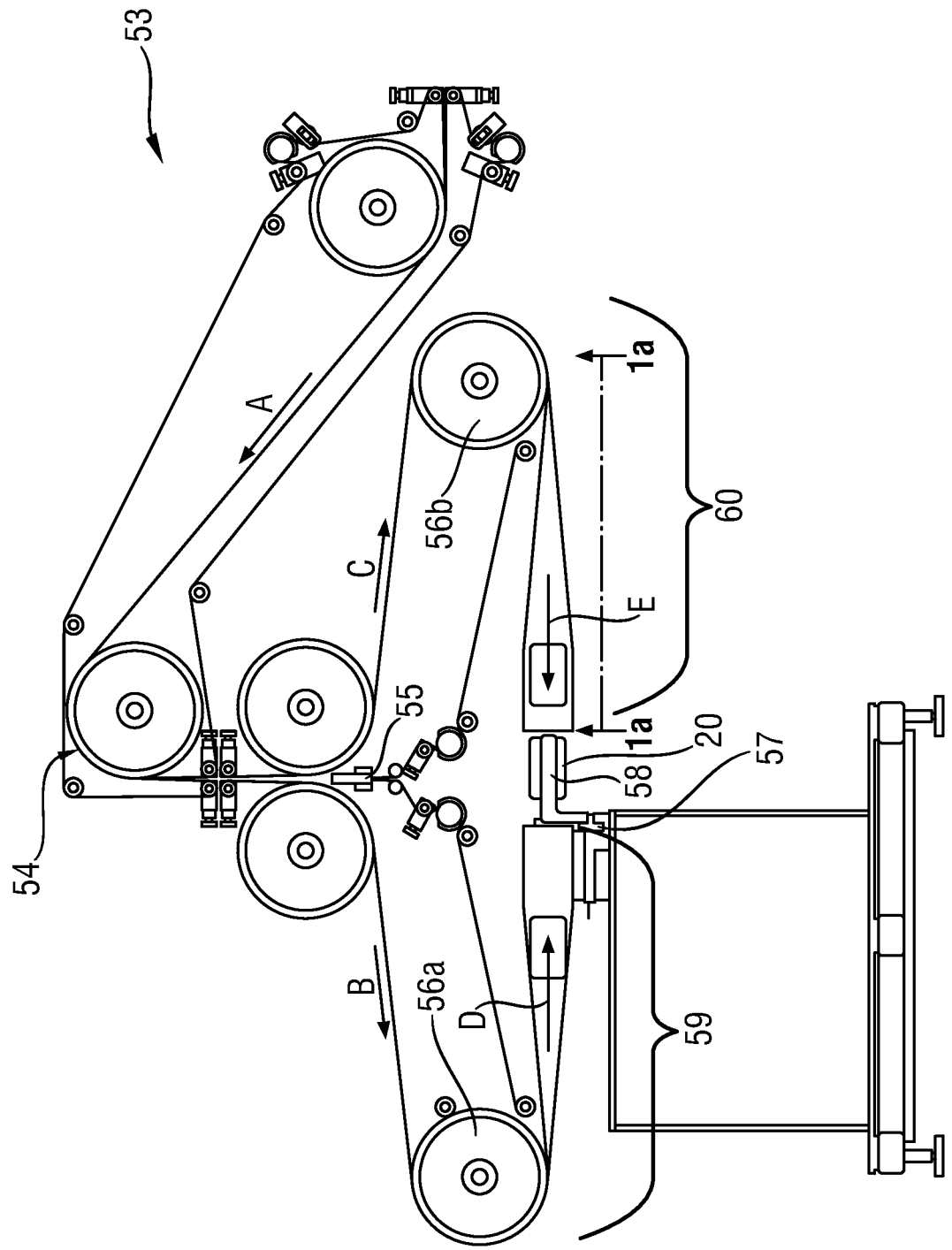
FIG. 5 is a schematic view of an exemplary embodiment of an apparatus for forming arrays of absorbent articles for subsequent packaging according to the present invention.

FIG. 5 is a schematic view of an exemplary embodiment of the apparatus 53 of the present invention which may be used to compile an array of absorbent articles 20 such as that shown in FIG. 4. Thus, as shown in FIG. 5, absorbent articles 20 may be provided to the apparatus along the direction of arrow A towards a diverter 55. This may be achieved by the infeeding roll 54. The absorbent articles may be provided to the diverter 55 on a support such as a conveyor belt. For example, absorbent articles 20 may travel between a pair of parallel conveyor belts in sequential fashion. Such conveyor devices are capable of providing individual absorbent articles to the diverter 55, usually in a folded, vertical position.

Absorbent articles are provided to a diverter 55 which may be controlled by sensors not shown in FIG. 5. The absorbent articles are diverted into two paths 59 and 60. One or more absorbent articles of a first plurality of absorbent articles may be routed to a first path 59 (indicated by arrows B and D in FIG. 5) while the access to the second path 60 is closed by the diverter 55. Then, alternately, after that one or more absorbent articles of the first plurality of absorbent articles has passed through a sensor located between the diverter 55 and the guide roll 56*a*, the diverter 55 may close the access to the first path 59 and open the access to the second path 60. One or more absorbent articles of a second plurality of absorbent articles may be then routed to the second path 60 (indicated by arrows C and E in FIG. 5). The first and second path have a direction different from each other.

The incoming path to the diverter 55 may be the same as the first or second path. However, the first and second path may have a direction different from the incoming path (or predetermined path).

Each path may have a guide roll 56*a* or 56*b* as shown in FIG. 5. Each path takes a substantially diverging direction along a first distance (indicated by arrows B or C) onto the guide rolls 56*a* and 56*b*. Then, these guide rolls permit for each path to take a substantially convergent direction along a second distance (indicated by arrows D or E) behind each guide roll. The guide rolls 56*a* and 56*b* facilitate a change of direction of the first and second path to allow the absorbent article to be delivered to the stacker 57.

The first distance (indicated by arrow B) of the first path 59 may be identical to the first distance (indicated by arrow C) in the second path 60. In the embodiment represented in FIG. 5, the second distance (indicated by arrow D) of the first path 59 may be identical to the second distance (indicated by arrow E) in the second path 60 (See for example FIG. 5).

The first and second distance of the first and second path (indicated by arrow B, C, D and E) may be identical. The guide rolls 56*a* and 56*b* may be therefore positioned symmetrically to the diverter 55.

The absorbent articles may travel along the first and second path at equal speed. Alternatively, the absorbent articles may travel at a higher speed along a first path compared to the absorbent articles travelling along the second path. Such a configuration may be desirable, e.g. if certain space constraints do not allow for the first and second path having the same length.

Alternatively, the overall length of the first path 59 may be different from the overall length in the second path 60 whereas the absorbent articles may have the same velocity in each path. This may be beneficial for forming arrays of absorbent articles with subunits consisting of one or more absorbent articles that are arranged in an identical orientation, followed by a neighboring subunit with a different number of absorbent articles arranged in an alternated orientation.

Thus, the processes of the present invention provide a high degree of flexibility to form different array configurations. The present invention may therefore comprise apparatus that can be adapted easily and quickly to provide different configurations of arrays of absorbent articles.

Providing the First and Second Plurality of Absorbent Articles to a Stacker

Figure 6:
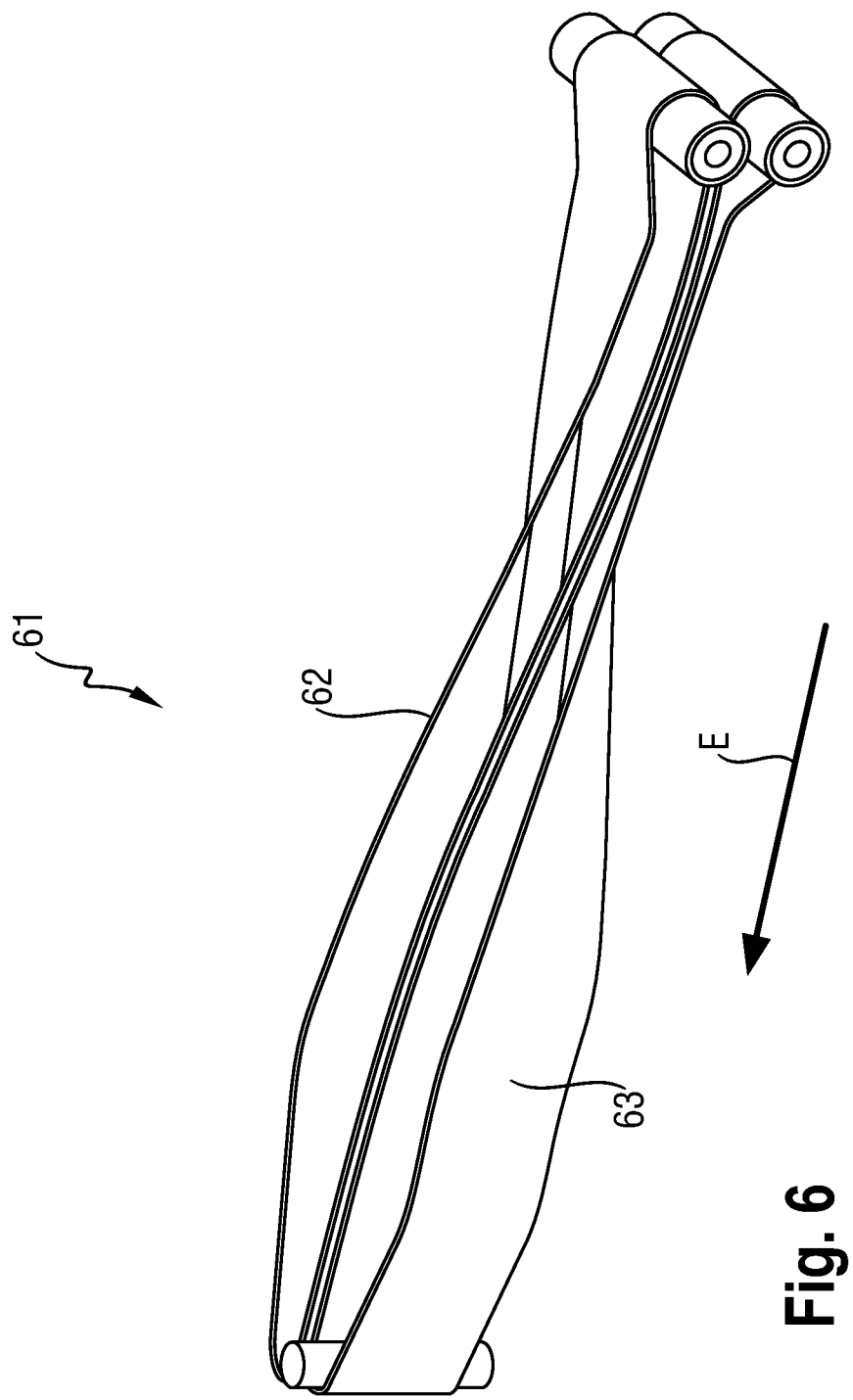
FIG. 6 is a perspective view of a path of twist belts used to twist absorbent articles, taken along the line 1*a*-1*a* of FIG. 5.

Each absorbent article after being diverted to the first or second path may be twisted in order to be introduced between two paddles 58 in the stacker 57. As shown in FIG. 6, after the guide rolls 56*a* and 56*b*, a path of twist belts 61 brings the absorbent articles into a vertical position. The absorbent article shown in FIG. 2 has a main surface 50. When an absorbent article 20 enters in the first path 59, the absorbent article 20 is typically in a horizontal position. Then, after the guide rolls 56*a* and 56*b*, twist belts 62 and 63 comprised by the first and second paths may bring the absorbent articles into a vertical position.

In the apparatus and processes of the present invention, the first and/or second plurality of absorbent articles while traveling along to the first or second path do not undergo any rotation to inverse the orientation of the first and/or second plurality of absorbent articles, such that the leading end (e.g. nose 47) of the absorbent article(s) and the trailing end (e.g. tail 48) of the absorbent article(s) are inverted.

Forming an Array of Absorbent Articles

Figure 7:
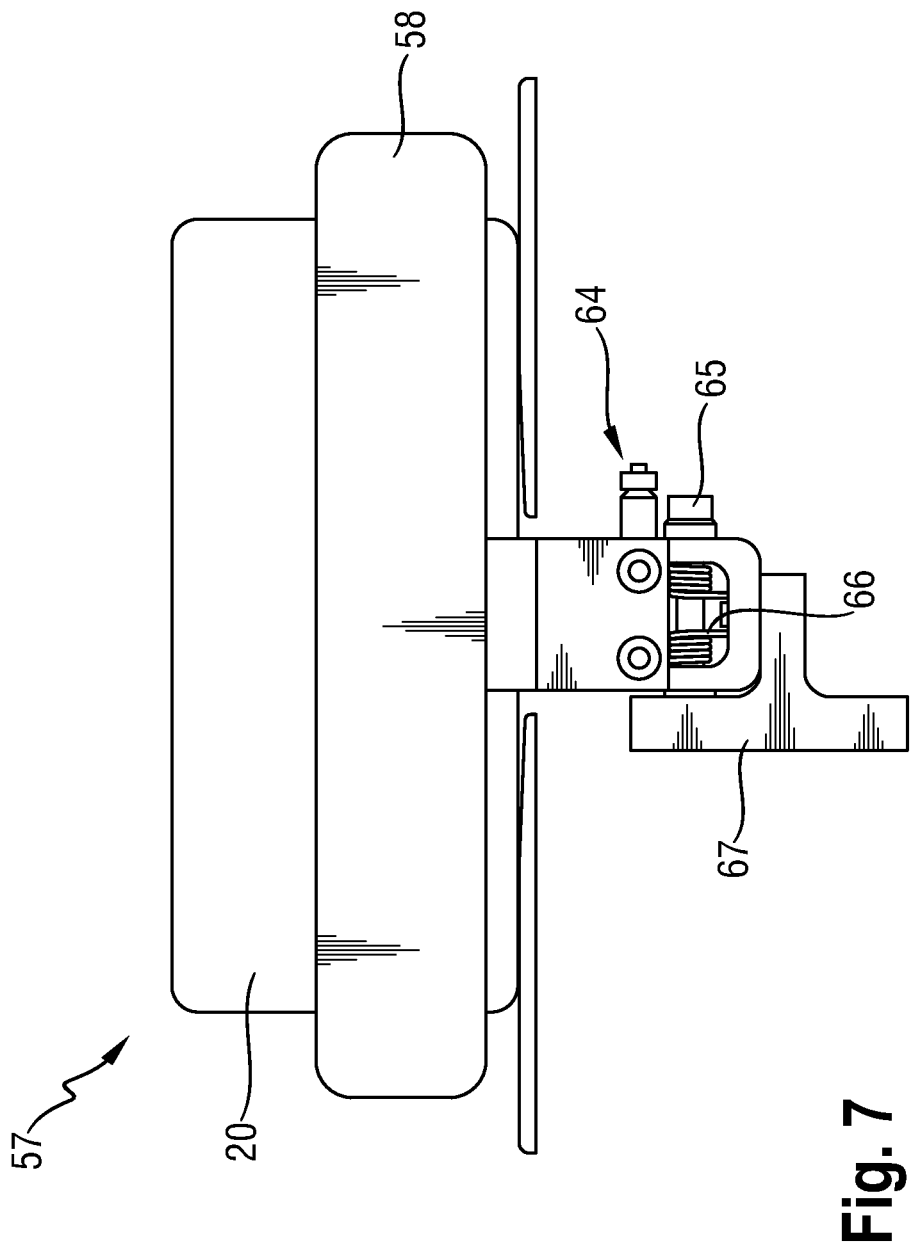
FIG. 7 is a side plan view of a paddle secured to a stacker of the exemplary embodiment of FIG. 5.
Figure 8:
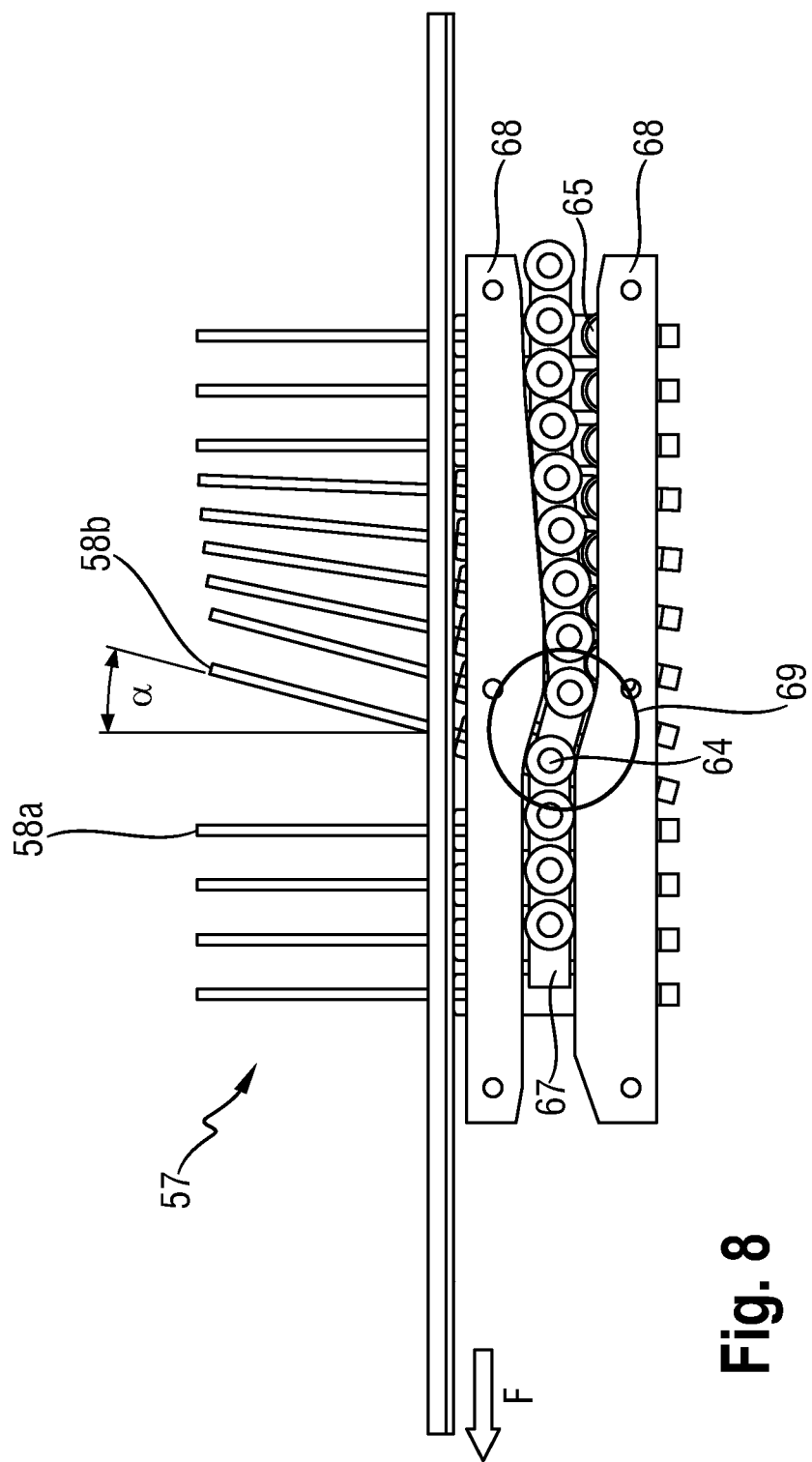
FIG. 8 is a side schematic view of a portion of the stacker, wherein paddles are bending outwardly.

The apparatus for forming arrays of absorbent articles for subsequent packaging generally comprises a stacker 57. The stacker 57 may include a plurality of paddles 58 secured to a support such as a chain 67 as shown in FIGS. 7 and 8. The paddles may be parallel to or arranged at an angle of up to 45 degrees or up to 20 degrees or up to 10 degrees to the direction of the first and second path. Paddles may be placed at equal distances from each other for receiving the absorbent articles as shown in FIG. 8. The stacker advances along a third path (indicated by arrow F), which has a direction different from the direction of the first and second path.

The region between two neighboring paddles 58 in the apparatus of FIG. 8 may define a compartment or pocket into which an absorbent article 20 may be delivered.

First, one or more advancing paddles 58 not yet in contact with an absorbent article may bend outwardly at an angle α up to 15 degrees, or up to 10 degrees, or up to 5 degrees relative to a vertical upright paddle position. The angle α has a value of 0 degree when the paddle 58*b* is parallel to the paddle 58*a*. This opening may be achieved by advancing a track roller 64 of the paddle 58*b* along a cam track 68, which comprises an angular portion 69. The angular portion 69 provides for the paddle 58*b* to pivot slightly around a pivoting shaft 65 at an angle α up to 15 degrees, or up to 10 degrees, or up to 5 degrees relative to a vertical upright paddle position.

Once an absorbent article has been deposited into a compartment formed between two neighboring paddles 58*a* and 58*b*, the neighboring paddles may be closed by straightening the paddle 58*b* back to an upright vertical position. For instance, straightening up a paddle may be controlled by a return spring 66 as illustrated in FIG. 7. The thus deposited absorbent article will travel within this compartment of the stacker 57 along a third path (indicated by arrow F) in FIG. 8.

Infeed Plates

Figure 9A:
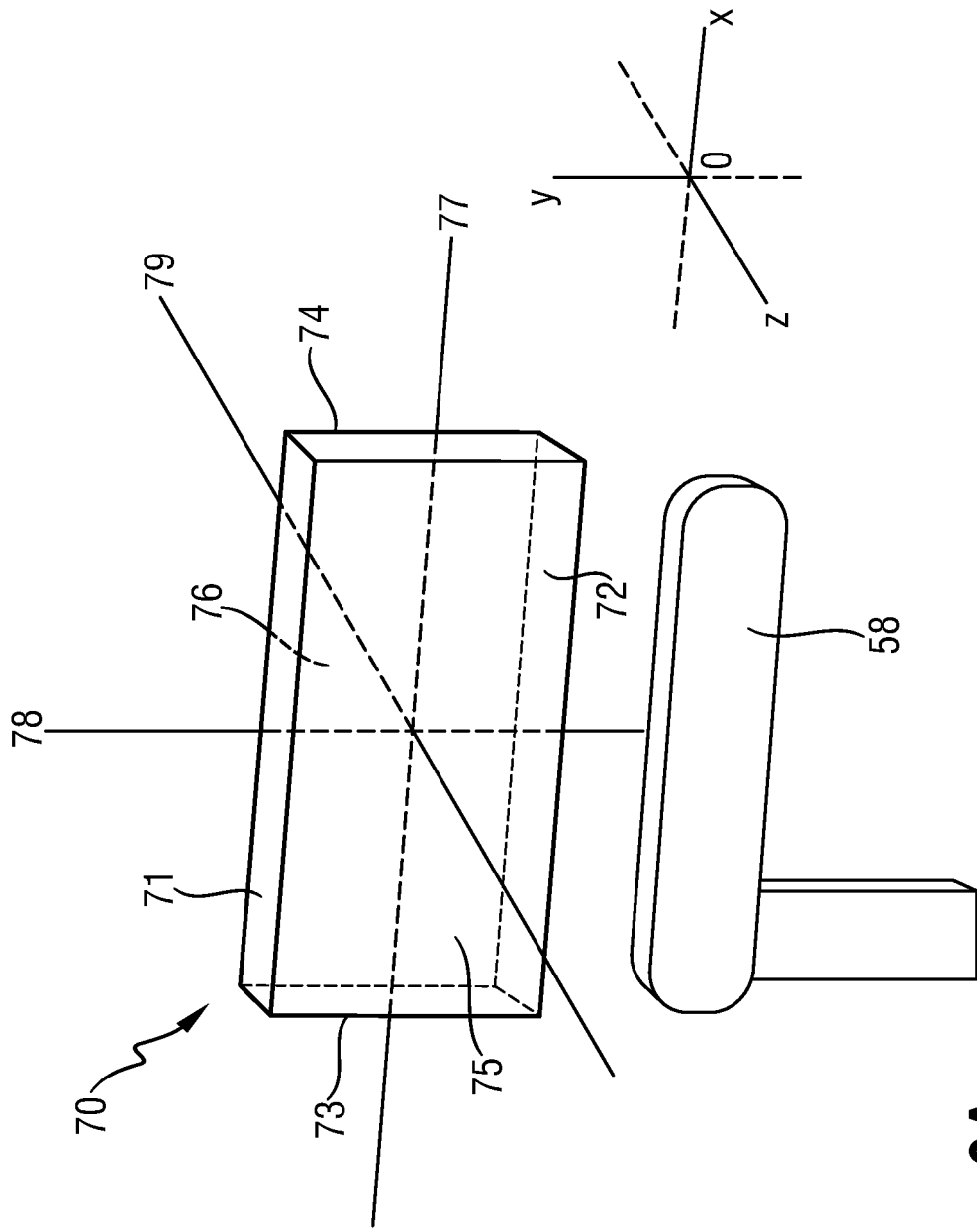
FIG. 9A is a schematic view of a "basic" infeed plate above a paddle secured to a stacker.

FIG. 9A is a schematic view of a "basic" infeed plate 70 above a paddle 58. The infeed plate is a component of the stacker. The infeed plate 70 may be made of suitable materials known in the art such as metal, or polymeric materials (e.g. Teflon). As illustrated in FIG. 9A, the infeed plate is bounded by three pairs of surfaces. For instance as shown in FIG. 9A, the infeed plate 70 may have a rectangular shape wherein all angles are right angles and opposite faces are equal. However, the shape of the infeed plate may take any other shape such as any hexahedron shapes (e.g. a cube), shapes with curved edges, elliptical shapes, rhomboid or trapezoid shapes.

The infeed plate has two main surfaces 75 and 76. The infeed plate may have an upper surface 71 and a lower surface 72. In addition, the infeed plate may have two side surfaces 73 and 74.

The infeed plate 70 has a length along a first horizontal axis 77, a height along a vertical axis 78 and a depth along a second horizontal axis 79. All axis 77-79 are perpendicular to each other.

As shown in FIG. 9B-13B, the infeed plate 80 may constantly be above the paddles 58 without any contact with the paddles of the stacker 57 upon movement of the infeed plate 80. Alternatively, the infeed plate 80 may go up and down between the paddles 58 while the array of absorbent articles is formed to let the paddles 58 advance along the third path.

Figure 9B:
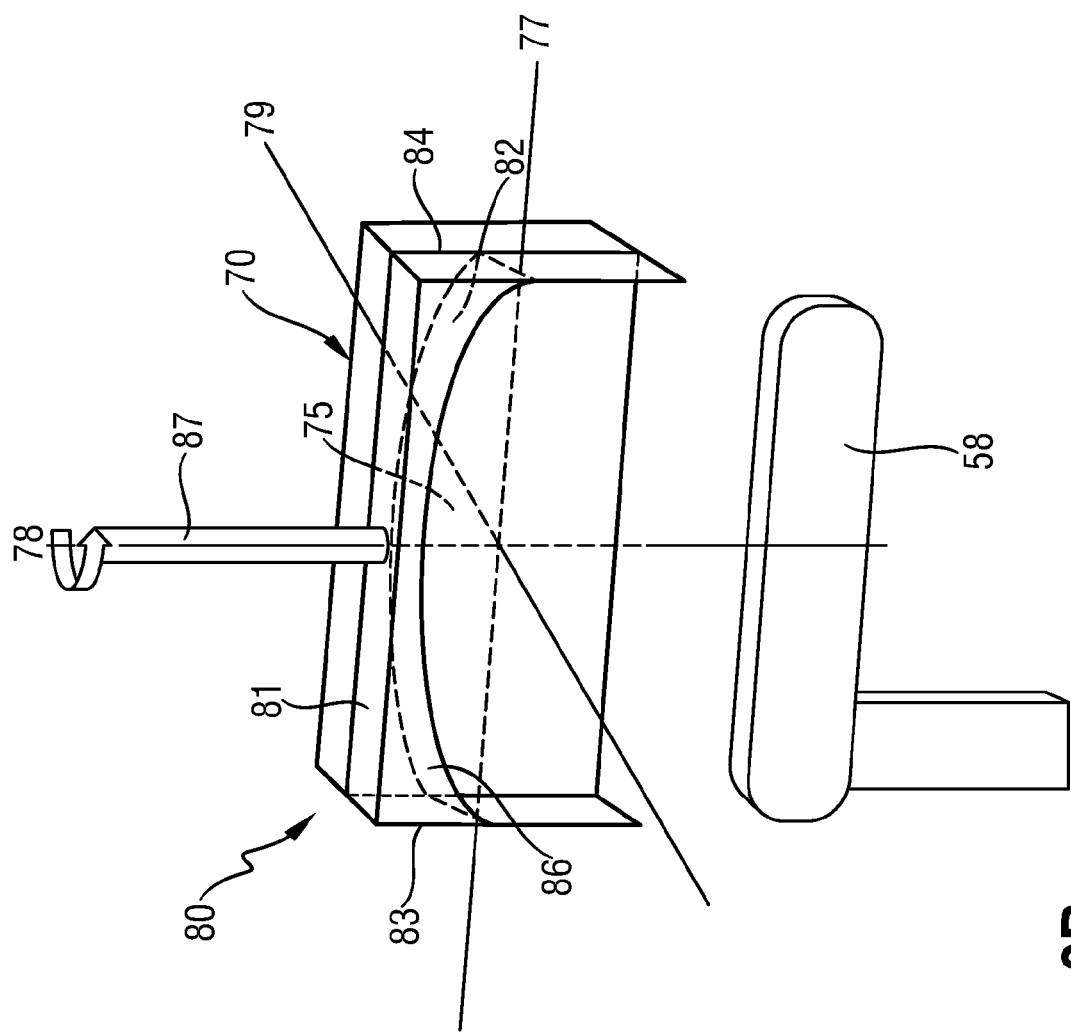
FIG. 9B is a schematic view of an infeed plate above a paddle secured to a stacker and attached at its upper surface to a pivoting shaft.
Figure 9C:
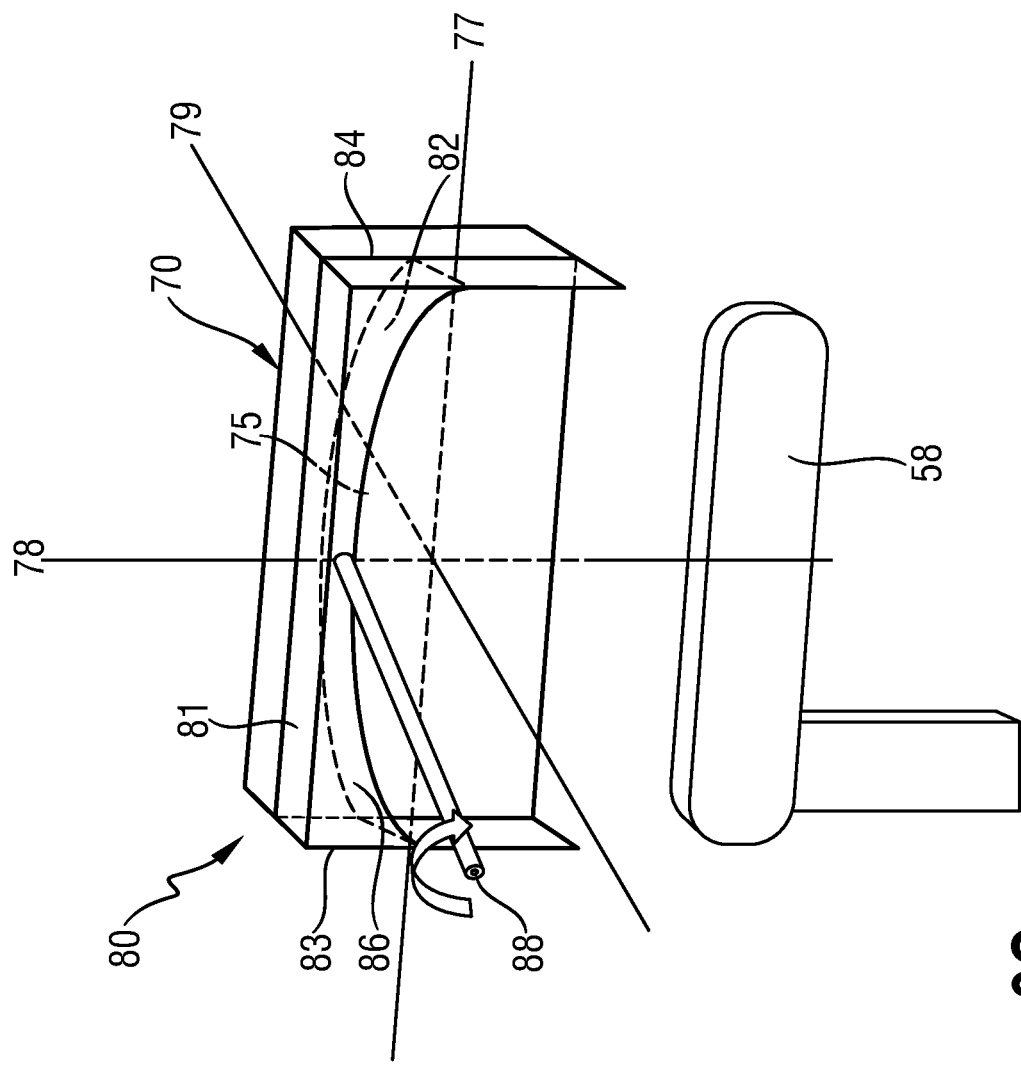
FIG. 9C is a schematic view of an infeed plate above a paddle secured to a stacker and attached at the front surface of the upper protrusion to a pivoting shaft.

FIGS. 9B and 9C are schematic views of an exemplary infeed plate 80. The infeed plate 80 can have an upper protrusion 82 which may be straight or curved, two side protrusions on the left and right sides 83 and 84 which may be straight or curved, an upper surface 81 which may be straight or curved and a main surface 75 which may be straight or curved. The upper protrusion 82 can have a front surface 86. The protrusions can be integral with the "basic" infeed plate 70 (shown in FIG. 9A) or may be separate pieces attached to the "basic" infeed plate 70.

The infeed plate 80 in FIG. 9B is attached at its upper surface 81 to a pivoting shaft 87 that is parallel to the vertical axis 78. The infeed plate 80 may therefore pivot around the shaft 87, e.g. at an angle γ ranging from −40 degrees to +40 degrees, or from −30 degrees to +30 degrees, or from −20 degrees to +20 degrees. The angle γ has a value of 0 degree when the main surface 75 of the infeed plate 80 is parallel to the paddle 58. The shaft 87 may be also connected to a drive means, such as a motor, to allow the infeed plate 80 to rotate.

FIG. 9C is a schematic view of an alternative infeed plate 80 wherein the infeed plate 80 is attached either at the main surface (not shown) or at the front surface 86 of the upper protrusion 82 to a pivoting shaft 88 that is either coincident with the second horizontal axis 79 or parallel to it. The shaft 88 may be also connected to a drive means, such as a motor, to allow the infeed plate 80 to rotate around the shaft 88, e.g. at an angle δ ranging from −90 degrees to +90 degrees, or from −80 degrees to +80 degrees, or from −70 degrees to +70 degrees. The angle δ has a value of 0 degree when the upper surface 81 of the infeed plate 80 is parallel to the surface (Oxz) or when the two side protrusions on the left and right sides 83 and 84 are in an upright vertical position.

FIGS. 12A and 12B are schematic views of an infeed plate which consist of first and second part 80a and 80b.

Each part of infeed plate 80a or 80b can have an upper protrusion 82a or 82b which may be straight or curved, a side protrusion on the left side 83a or the right side 84b which may be straight or curved, an upper surface 81a or 81b and a main surface 75a or 75b. Each upper protrusion 82a or 82b can have a front surface 86a or 86b. The first part of infeed plate 80a may be attached at its upper surface 81a to a shaft 87a that is parallel to the vertical axis 78. The same applies for the second part of infeed plate 80b as shown in FIGS. 12A and 12B.

In FIG. 12A, the first and second part of infeed plate 80a and 80b may slide up and down in a direction substantially parallel to the vertical axis 78, whereas in FIG. 12B, the first and second part of infeed plate 80a and 80b may slide back and forth in a direction substantially parallel to the second horizontal axis 79. In FIG. 12B, for instance, the sliding back and forth of the parts of infeed plate 80a and 80b is achieved by the sliding of a carriage 89a or 89b along a linear guide 90a or 90b, which is substantially parallel to the second horizontal axis 79.

Pivoting Infeed Plates

Figure 10A:
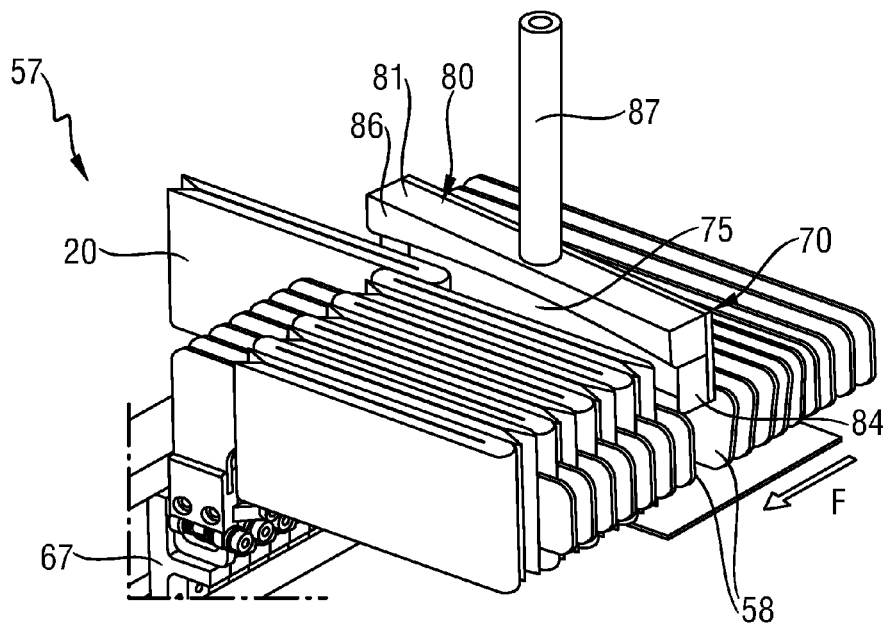
FIG. 10A is a perspective view of a portion of the stacker, wherein a diaper is provided from the first path.
Figure 10B:
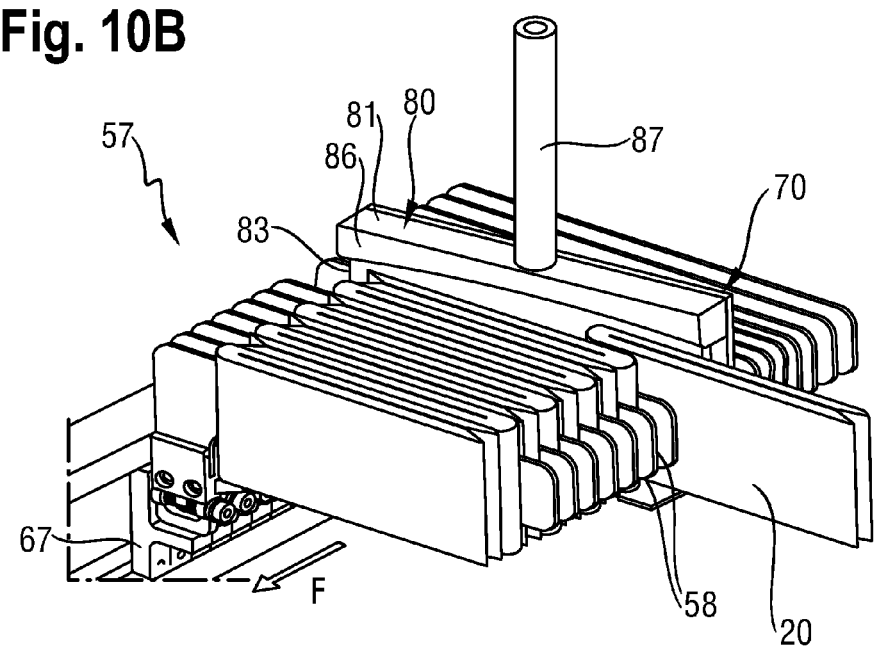
FIG. 10B is a perspective view of a portion of the stacker, wherein a diaper is provided from the second path.
Figure 11:
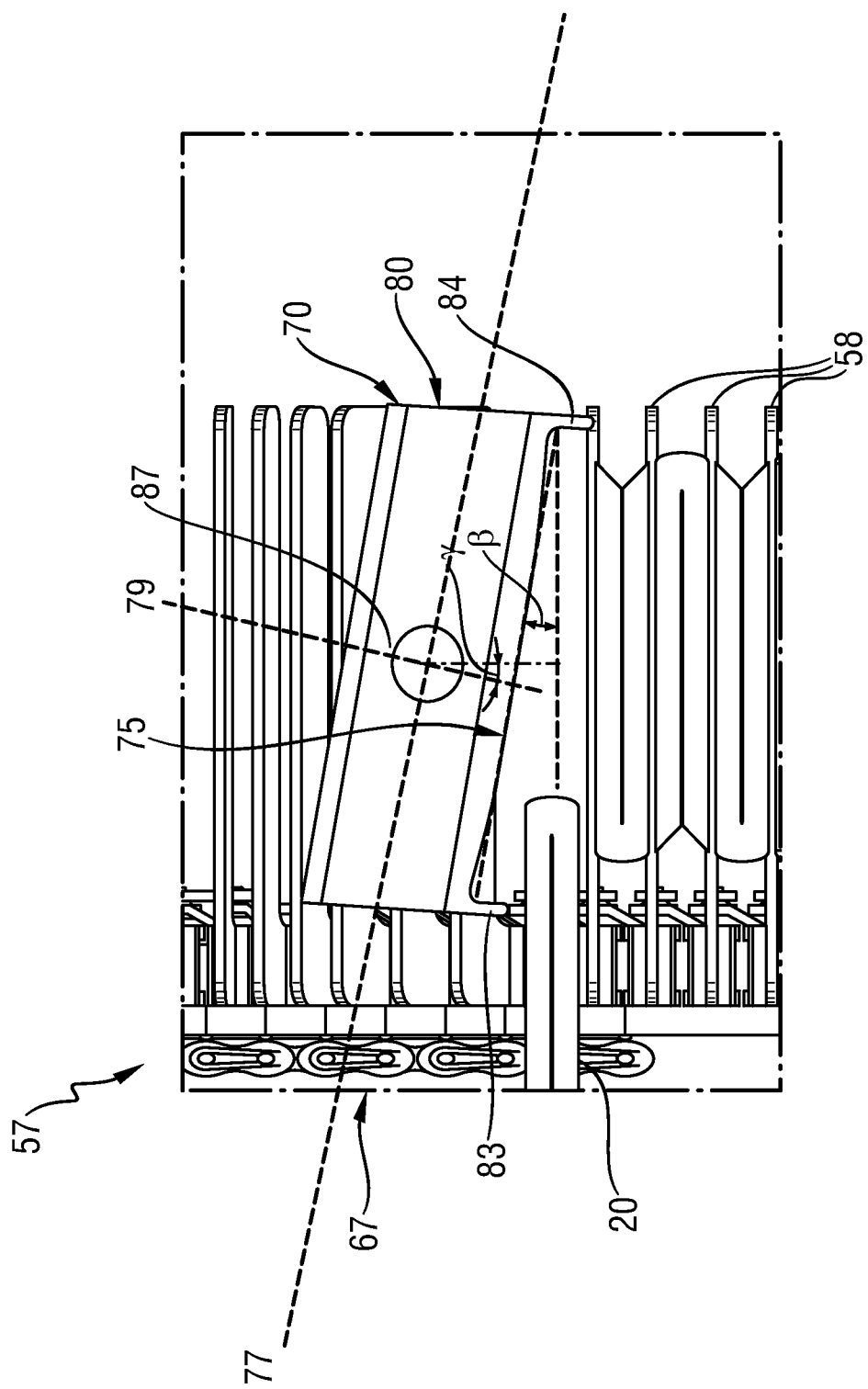
FIG. 11 is a top schematic view of a portion of the stacker, wherein a diaper delivered by the first path is introduced between two neighboring paddles.
Figure 13B:
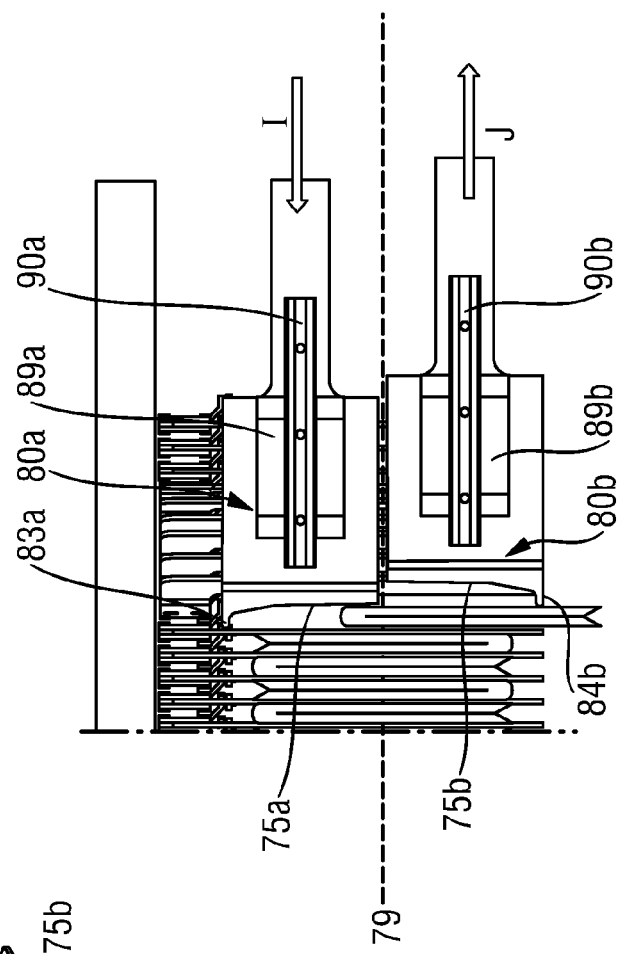
FIG. 13B is a top schematic view of a portion of the stacker, wherein a diaper is provided from the second path and wherein the stacker comprises an infeed plate which consist of first and second part that may slide back and forth.
Figure 13A:
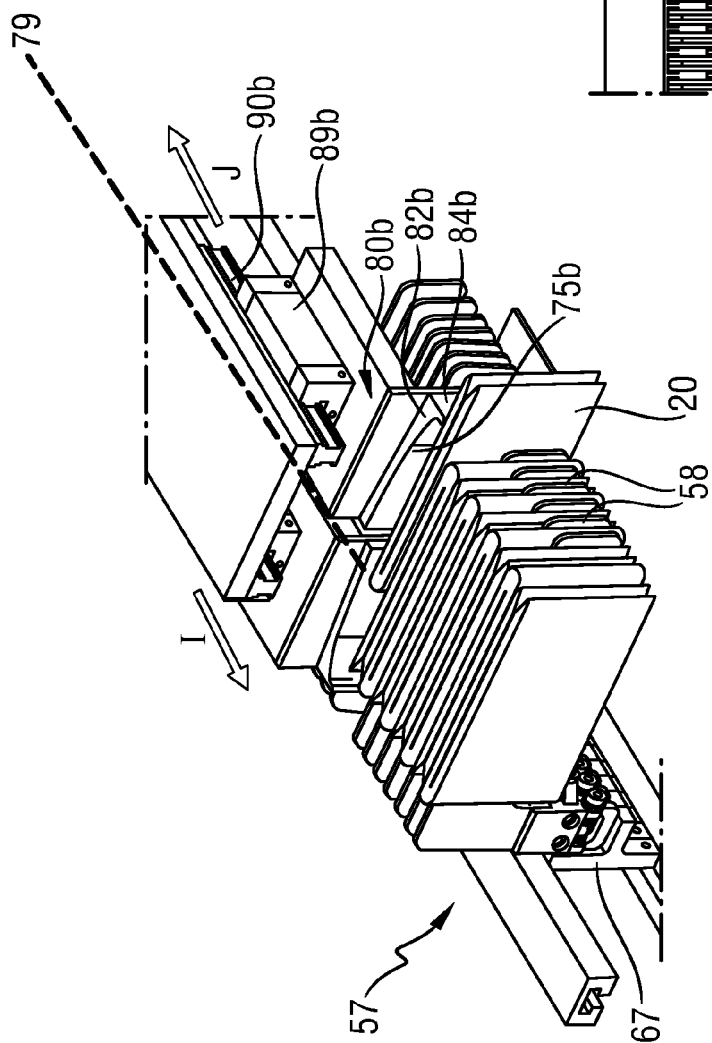
FIG. 13A is a perspective view of a portion of the stacker, wherein a diaper is provided from the second path and wherein the stacker comprises an infeed plate which consist of first and second part that may slide back and forth.

First and second plurality of absorbent articles are provided from the first and second path to the stacker 57. One absorbent article is introduced between two neighboring paddles 58 from one side of the stacker 57, as shown in FIGS. 10A, 10B and 11. The neighboring paddles are closed by straightening neighboring paddles into an upright vertical position. Upon straightening up the paddles, the absorbent article is securely held and positioned between two paddles.

As illustrated in FIG. 10A, an absorbent article 20 provided from the first path 59 is placed between two neighboring paddles 58 via one side of the stacker 57. As illustrated in FIG. 10B, an absorbent article 20 provided from the second path 60 is placed between two neighboring paddles 58 via another opposite side of the stacker 57.

In order to allow infeed from both sides of the stacker 57 in an alternating fashion, the infeed plate 80 is pivoting around the shaft 87, e.g. at an angle γ ranging from −40 degrees to +40 degrees, or from −30 degrees to +30 degrees, or from −20 degrees to +20 degrees.

FIG. 11 is a top plan view of a portion of the stacker 57, wherein an absorbent article 20 provided by the first path 59 is introduced between two neighboring paddles 58. The main surface 50 of the absorbent article 20 in a vertical position may be substantially parallel to the paddles 58 or at an angle of up to 45 degrees, or up to 20 degrees or up to 10 degrees. Upon entry of an absorbent article 20 provided by the first path 59, the infeed plate 80 has rotated around the shaft 87, e.g. at an angle γ ranging up to +40 degrees to be positioned in such a way to allow an advancing absorbent article 20 provided by the first path 59 to be introduced between two neighboring paddles 58.

In FIG. 11, when the absorbent article 20 which has entered between the paddles 58 and the infeed plate 80 is advancing towards the side protrusion 84 of the infeed plate 80, the absorbent article is slowed down due to friction forces created between the main surface 75 of the infeed plate 80 and the main surface 50 of the absorbent article 20. First, the nose 47 of the absorbent article 20 contacts the main surface 75 of the pivoting infeed plate 80, e.g. at an angle β ranging from 5 degrees to 40 degrees, or from 5 degrees to 30 degrees, or from 5 degrees to 20 degrees. The nose 47 of the absorbent article may contact the upper protrusion 82, which avoids that the absorbent article is inadvertently ejected out of the compartment. Then, the main surface 50 of the absorbent article 20 slides against the main surface 75 of the infeed plate 80 and is stopped by the side protrusion 84 of the infeed plate 80 as shown in FIG. 11. The absorbent article 20 is decelerated progressively by the infeed plate 80, which avoids any damage of the absorbent article.

However, if a bi-folded absorbent article 20, such as a bi-folded diaper, a bi-folded sanitary napkin and a bi-folded panty liner delivered between two neighboring paddles 58 is entering by its tail 48, the bi-folded absorbent article 20 may fold and crimp. Therefore, bi-folded absorbent articles 20 should preferably enter the stacker 57 by their noses 47, as the nose portion is generally thicker and/or more stable than the tail 48. Apparently, for e.g. tri-folded absorbent articles, such differentiation is not needed, as they do not have a nose which is substantially different from the tail regarding thickness and/or stability.

Subsequently, the infeed plate 80 may pivot around the shaft 87, e.g. at an angle γ ranging from −40 degrees to +40 degrees, or from −30 degrees to +30 degrees, or from −20 degrees to +20 degrees to allow an advancing absorbent article 20 provided by the second path 60 to be introduced between two neighboring paddles 58 in a similar manner as an absorbent article 20 provided by the first path 59.

(As shown in FIG. 9C), when the infeed plate 80 is attached to a shaft 88 such that the shaft 88 is parallel to the second horizontal axis 79, the infeed plate 80 may rotate around the shaft 88, e.g. at an angle δ ranging from −90 degrees to +90 degrees, or from −80 degrees to +80 degrees, or from −70 degrees to +70 degrees.

Upon entry of an absorbent article 20 provided by the first path 59, the infeed plate 80 has rotated at an angle δ ranging e.g. up to +90 degrees to be positioned in such a way to allow an advancing absorbent article 20 provided by the first path 59 to be introduced between two neighboring paddles 58.

When the absorbent article 20 delivered to the first path 59 is advancing towards the upper protrusion 82 of the infeed plate 80 which due to the current position of the infeed plate 80 is indeed facing sideways, the absorbent article is slowed down due to friction forces created between the main surface 75 of the infeed plate 80 and the main surface 50 of the absorbent article 20. First, the nose 47 of the absorbent article contacts the main surface 75 of the infeed plate 80, e.g. at an angle ranging from 5 degrees to 40 degrees, or from 5 degrees to 30 degrees, or from 5 degrees to 20 degrees. The main surface 50 of the absorbent article 20 slides against the main surface 75 of the infeed plate 80 and is stopped by either the upper protrusion 82 and/or one of the side protrusions 83 or 84, depending on how far the infeed plate 80 has been rotated.

Subsequently, the infeed plate 80 may pivot around the shaft 88 at an angle δ ranging e.g. from −90 degrees to +90 degrees, or from −80 degrees to +80 degrees, or from −70 degrees to +70 degrees to allow an advancing absorbent article 20 provided by the second path 60 to be introduced between two neighboring paddles 58 in a similar manner as an absorbent article 20 provided by the first path 59.

In both alternatives illustrated in FIGS. 9B and 9C, while subsequent absorbent articles enter the stacker 57, the infeed plate 80 may or may not pivot. If the infeed plate 80 is not rotating, several absorbent articles provided by the same path can be introduced at the same side of the stacker 57. This may be beneficial for forming arrays 52 of absorbent articles with subunits of absorbent articles 20 arranged in an identical, side by side orientation followed by a subunit of absorbent articles 20 arranged in an alternating orientation. The number of absorbent articles in each group may be different. For instance, the absorbent articles in the array may be arranged two by two, three by three or one by two in subunits. Different configurations of arrays may be therefore achieved.

Sliding Portions of Infeed Plates

In FIG. 12A, upon entry of an absorbent article 20 provided by the second path 60, the first part of the infeed plate 80a slides down along the vertical axis 78 (in a direction indicated by arrow G) in order to stop the advancing absorbent article 20. Simultaneously, the second part of the infeed plate 80b slides up along the vertical axis 78 (in a direction indicated by arrow H) to allow the advancing absorbent article 20 provided by the second path 60 to be introduced between two neighboring paddles 58.

In FIG. 12A, when the absorbent article 20 coming from the second path 60 is advancing towards the side protrusion 83a of the first part of the infeed plate 80a, the absorbent article 20 is slowed down due to friction forces created between the main surface 75a of the part of the infeed plate 80a and the main surface 50 of the absorbent article 20. First, the nose 47 of the absorbent article 20 contacts the main surface 75a of the part of the infeed plate 80a, e.g. at an angle β ranging from 5 degrees to 40 degrees, or from 5 degrees to 30 degrees, or from 5 degrees to 20 degrees. The nose 47 of the absorbent article 20 may contact the upper protrusion 82a, which avoids that the absorbent article is inadvertently ejected out of the compartment Then, the main surface 50 of the absorbent article 20 slides against the main surface 75a of the first part of the infeed plate 80a and is stopped by the side protrusion 83a of the first part of the infeed plate 80a.

In FIG. 12A, the first part of the infeed plate 80a may then slide up along the vertical axis 78 (in a direction indicated by arrow H), to allow an advancing absorbent article 20 provided by the first path 59 to be introduced between two neighboring paddles 58 in a similar manner as an absorbent article 20 provided by the second path 60. Simultaneously, the second part of the infeed plate 80b may slide down along the vertical axis 78 (in a direction indicated by arrow G) to allow the absorbent article 20 coming from the first path 59 to be decelerated and stopped at the side protrusion 84b of the second part of the infeed plate 80b.

In FIG. 12B-13B, upon entry of an absorbent article 20 provided by the second path 60, the first part of the infeed plate 80a slides forward along the second horizontal axis 79 (in a direction indicated by arrow I) in order to stop the advancing absorbent article 20. Simultaneously, the second part of the infeed plate 80b slides backwards along the second horizontal axis 79 (in a direction indicated by arrow J) to allow the advancing absorbent article 20 provided by the second path 60 to be introduced between two neighboring paddles 58.

In FIG. 12B-13B, when the absorbent article 20 coming from the second path 60 is advancing towards the side protrusion 83a of the first part of the infeed plate 80a, the absorbent article 20 is slowed down due to friction forces created between the main surface 75a of the part of the infeed plate 80a and the main surface 50 of the absorbent article 20. First, the nose 47 of the absorbent article 20 contacts the main surface 75a of the part of the infeed plate 80a, e.g. at an angle β ranging from 5 degrees to 40 degrees, or from 5 degrees to 30 degrees, or from 5 degrees to 20 degrees. The nose 47 of the absorbent article 20 may contact the upper protrusion 82a of the first part of the infeed plate 80a, which avoids that the absorbent article is inadvertently ejected out of the compartment Then, the main surface 50 of the absorbent article 20 slides against the main surface 75a of the first part of the infeed plate 80a and is stopped by the side protrusion 83a of the first part of the infeed plate 80a.

In FIG. 12B-13B, the first part of the infeed plate 80a may then slide backwards along the second horizontal axis 79 (in a direction indicated by arrow J), to allow an advancing absorbent article 20 provided by the first path 59 to be introduced between two neighboring paddles 58 in a similar manner as an absorbent article 20 provided by the second path 60. Simultaneously, the second part of the infeed plate 80b may slide forward along the second horizontal axis 79 (in a direction indicated by arrow I) to allow the absorbent article 20 coming from the first path 59 to be decelerated and stopped at the side protrusion 84b of the second part of the infeed plate 80b.

In both cases illustrated in FIGS. 12A and 12B, while subsequent absorbent articles enter the stacker 57, the first and second part of infeed plate 80a and 80b may or may not slide up and down, or back and forth. If the parts of infeed plate 80a and 80b do not slide up and down, or back and forth, several absorbent articles provided by the same path can be introduced at the same side of the stacker 57.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of forming arrays of absorbent articles with varying orientations comprising the steps of:
   (a) advancing absorbent articles along a predetermined path;
   (b) using a diverter, diverting a first plurality of absorbent articles to a first path and diverting a second plurality of absorbent articles to a second path, wherein the first path and the second path have a different direction from each other;
   (c) providing the first plurality of absorbent articles and the second plurality of absorbent articles to a stacker adapted to receive absorbent articles from the first path and the second path;
   (d) forming an array of absorbent articles from the first plurality of absorbent articles and the second plurality of absorbent articles in the stacker, wherein at least one of the absorbent articles has a first orientation and at least one of the absorbent articles has a second orientation within the array, the first orientation and the second orientation being different from each other;
   (e) advancing the array of absorbent articles along a third path, wherein the third path has a direction different from the direction of the first path and the second path;
   (f) introducing an absorbent article between two paddles such that main surfaces of the absorbent articles are substantially parallel to the paddles and at an angle from about 10 degrees to about 40 degrees to an infeed plate;
   (g) slowing the absorbent article due to friction forces created between a main surface of the infeed plate and one of the main surfaces of the absorbent article; and
   (h) stopping the absorbent article with a portion of the infeed plate.

2. The process of claim 1, wherein the first plurality of absorbent articles is provided to the stacker from a first direction, and the second plurality of absorbent articles is provided to the stacker from a second direction, wherein the first direction is different from the second direction.

3. The process of claim 2, wherein the first plurality of absorbent articles has the first orientation and the second plurality of absorbent articles has the second orientation in the array of absorbent articles.

4. The process of claim 3, wherein the first plurality of absorbent articles is oriented about 180 degrees relative to the second plurality of absorbent articles in the array.

5. The process of claim 1, wherein the step d) further comprises:
   (a) opening up two neighboring paddles by bending outwardly at least one of the paddles,
   (b) introducing one of the absorbent articles delivered by the first or second path between the two paddles,
   (c) stopping the one absorbent article with an infeed plate, wherein the infeed plate is:
      i) pivoting, or
      ii) comprising a first part and a second part, the first and second part sliding up and down, or back and forth,
   (d) closing the neighboring paddles by straightening the at least one paddle relative to its neighboring paddle.

6. The process claim 1, further comprising directing the absorbent articles using an infeeding roll to the diverter along a predetermined path; and allowing one or more absorbent articles of the first plurality of absorbent articles to be routed in the first path while the second path is closed and alternately closes the first path to allow one or more absorbent articles of the second plurality of absorbent articles to be routed in the second path.

7. The process of claim 1, wherein the first path and the second path each have a guide roll to facilitate a change of direction within the first path and the second path.

8. The process of claim 7, wherein the first path and the second path define substantially diverging directions along a first distance onto the guide roll, and wherein from the guide roll, the first path and the second path define substantially convergent directions along a second distance.

9. A process of forming arrays of absorbent articles with varying orientations comprising the steps of:
   (a) providing a stacker, the stacker comprising a plurality of paddles placed at equal distances for receiving the absorbent articles;
   (b) opening up two neighboring paddles by bending outwardly at least one of the paddles;
   (c) introducing the absorbent articles delivered from two substantially opposite directions onto the stacker;
   d) stopping the absorbent article by an infeed plate, wherein the infeed plate is:
      i) pivoting, or
      ii) comprising a first and second part, the first and second part sliding up and down, or back and forth,
   (e) closing the neighboring paddles by straightening at least one paddle relative to its neighbor; and
   (f) forming an array of absorbent articles by repeating steps (b) through (e).

10. An apparatus for forming arrays of absorbent articles comprising:
   a diverter for diverting the absorbent articles to route a first plurality of absorbent articles to a first path and a second plurality of absorbent articles to a second path, wherein the first path and the second path have a direction different from each other;
   a stacker for receiving the first plurality of absorbent articles and the second plurality of absorbent articles delivered from the first and second path, wherein the stacker is adapted to form an array of absorbent articles from the first plurality of absorbent articles and the second plurality of absorbent articles, such that one or more than one of the absorbent articles has a first orientation and one or more than one of the absorbent articles has a second orientation within the array, the first and second orientations being different from each other,
   a third path along which the array of absorbent articles is advanced, wherein the third path has a direction different from the direction of the first and second paths, and wherein in the stacker, a plurality of paddles are placed for receiving the absorbent articles, wherein an infeed plate is placed above the paddles without any contact with the paddles when pivoting or sliding.

11. The apparatus of claim 10 wherein the infeed plate is:
i) pivoting, or
ii) comprising a first and second part, the first and second part sliding up and down, or back and forth.

12. The apparatus of claim 10, wherein the stacker further comprises a support, wherein the paddles are secured to the support, the support adapted to advance along the third path.

13. The apparatus of claim 10, wherein the absorbent articles are folded articles.

* * * * *